(12) United States Patent
Wang et al.

(10) Patent No.: US 7,430,276 B2
(45) Date of Patent: Sep. 30, 2008

(54) LOW DOSE X-RAY MAMMOGRAPHY METHOD

(75) Inventors: Chia-Gee Wang, Millwood, NY (US); Thomas Vullo, Brooklyn, NY (US)

(73) Assignee: Nanodynamics-88, New York, NY (US)

( * ) Notice: Subject to any disclaimer, the term of this patent is extended or adjusted under 35 U.S.C. 154(b) by 0 days.

(21) Appl. No.: 11/065,595

(22) Filed: Feb. 24, 2005

(65) Prior Publication Data

US 2005/0185756 A1    Aug. 25, 2005

Related U.S. Application Data

(60) Provisional application No. 60/547,639, filed on Feb. 25, 2004.

(51) Int. Cl.
A61B 6/00    (2006.01)
G01N 23/04    (2006.01)
H01J 35/08    (2006.01)

(52) U.S. Cl. .................. 378/62; 378/37; 378/121; 378/143; 600/431

(58) Field of Classification Search ............. 378/37, 378/121, 140, 143, 144, 5, 16, 98.9, 98.11, 378/124, 62; 600/425, 431
See application file for complete search history.

(56) References Cited

U.S. PATENT DOCUMENTS

| 5,044,001 | A | | 8/1991 | Wang |
| 5,111,828 | A | * | 5/1992 | Kornberg et al. ............ 600/567 |
| 5,593,990 | A | * | 1/1997 | D'Amato .................. 514/235.2 |
| 5,627,871 | A | | 5/1997 | Wang |
| 6,480,565 | B1 | * | 11/2002 | Ning ............................ 378/37 |
| 6,714,621 | B2 | * | 3/2004 | Rick et al. ................ 378/98.12 |
| 2005/0084060 | A1 | * | 4/2005 | Seppi et al. .................... 378/5 |
| 2005/0123093 | A1 | * | 6/2005 | Lawaczeck et al. ...... 378/98.11 |

OTHER PUBLICATIONS

B. D. Cullity and S. R. Stock. Elements of X-Ray Diffraction, third edition (Upper Saddle River, NJ: Prentice Hall, 2001).*
Noel Weidner et al., "Tumor Angiogenesis and Metastasis—Correlation in Invasive Breast Carcinoma," The New England Journal of Medicine, vol. 324, 1991, 1-8.*
Breast cancer-induced angiogenesis: multiple mechanisms and the role of the microenvironment, Nancy Boudreau and Connie Myers, Breast Cancer Research vol. 5, No. 3 p. 140-146.
Angiogenesis in cancer and other diseases, Peter Carmeliet and Rakesh Jain, Nature vol. 407, Sep. 14, 2000, pp. 249-257.
Tumor angiogenesis and metastasis—correlation in invasive breast carcinoma, Weidner, Semple, Welch, Folkman; N Engl J Med. Jan. 3, 1991; 324(1):1-8.
The role of angiogenesis in tumor growth; Folkman; Semin Cancer Biol. Apr. 1992; 3(2):65-71.

* cited by examiner

*Primary Examiner*—Allen C. Ho
(74) *Attorney, Agent, or Firm*—Ladas & Parry LLP (57) ABSTRACT

A mammography method images breast tissue with an end window X-ray transmission tube to detect the presence of neovascular micro-vessels as defining vascular structure associated with a suspect tumorous mass. A kit therefor has a high-efficiency, end window X-ray transmission tube and a supply of a contrast agent.

10 Claims, 7 Drawing Sheets

Figure 5
The Emission Spectrum of an End-Window Moly Target

LOW DOSE X-RAY MAMMOGRAPHY METHOD

This application claims the benefit of U.S. Provisional Application No. 60/547,639 filed Feb. 25, 2004, and incorporates the same by reference.

BACKGROUND OF THE INVENTION

The present invention relates to a mammography method and kit.

An X-ray transmission tube having a target including a thin metal coating such as silver on a substrate such as beryllium is described in U.S. Pat. No. 5,044,001 issued to Chia-Gee Wang on Aug. 27, 1991, the disclosure of which is incorporated herein by reference. An X-ray transmission tube having a target including a thin metal coating on a substrate such as beryllium is described in U.S. Pat. No. 5,627,871, issued to Chia-Gee Wang on May 6, 1997, the disclosure of which is incorporated herein by reference. In this patent a high efficiency transmission tube is designed so that the peak energy of the electron beam is set at about 3 times the K-absorption edge of the target material. Generation of monochromatic or characteristic X-rays of high flux density is disclosed by Wang in his two patents.

DETAILED DESCRIPTION OF THE INVENTION

One in eight women in the U.S. may develop breast cancer in their lifetimes. If detected early, breast cancer is highly curable, with a 5-year survival rate of 96%. Although mammography is the standard-of-care for early detection, it suffers from the following problems:

- The possibility of incurring radiation-induced carcinoma;
- Substantial rates of false positives and false negatives;
- Poor image quality for thick and dense breast tissues; and/or
- Cannot distinguish between a benign and malignant tumor growth.
- Women under 50 are generally not routinely examined by mammography because the risk/benefit considerations are unfavorable to them except under special situations.

A novel mammography system developed to provide the following improvements is highly desirable:

- The dose per view for a mammogram can be decreased by more than an order of magnitude in order to drastically reduce the risk of radiation-induced carcinoma;
- The resolution is greatly improved;
- The presence or absence of carcinoma becomes much easier to determine by a radiologist, with decreased incidences of false positives and false negatives;
- There is improved ability to discriminate between malignant and benign masses, greatly reducing the need for biopsy;
- The system is more user-friendly to patients, including those with thick and dense breast tissue; and/or
- The mammography system can be produced at a greatly reduced cost.

X-ray mammography has for many years been the gold standard for identifying abnormalities, including, for example, calcifications and masses in breast tissue. Variations in soft tissues will result in differing X-ray penetration depths and attenuations for a particular photon energy. For the specific profile of X-ray photon energies used in mammography, generally greater than 96% of the X-ray fluence is absorbed by the breast tissue and less than 4% will reach the film or digital imager. Thus, slight differences in X-ray transmission resulting from variations in tissue absorption can still provide for sufficient image contrast.

Digital mammography allows for software manipulations and improved image contrast. Here, a higher $kV_p$ can be used so that a larger fraction of the X-ray fluence can reach the digital detector. This results in a reduced total fluence and reduced LET (linear energy transfer) to the breast tissue and a lower dose by about 20%. In general, the radiation dose to the 4-5 cm compressed breast is approximately 150 mR per view. The X-ray tube typically has a molybdenum target and its voltage may vary from 23-28 $kV_p$. Using a higher $kV_p$ without digital manipulation would reduce the dose, but result in much reduced image contrast.

SUMMARY OF THE INVENTION

A mammography method is provided in accordance with the invention, which comprises imaging breast tissue with an end window X-ray transmission tube and defining vascular structure associated with a suspect tumorous mass to detect the presence of neovascular micro-vessels. In an embodiment of the invention an X-ray contrast agent is administered prior to the imaging. The invention also provides a kit for mammography comprising a high-efficiency, end window X-ray transmission tube and a supply of a contrast agent, wherein said tube comprises a target made of a metal selected to produce X-ray line-emissions having an energy selected for absorption by an element of said contrast agent.

If the soft tissue contrast in a mammogram were the only concern, then current efforts in the improvement of digital imagers towards higher sensitivity, better resolution, and more effective software manipulation to help obtain the desired image information are indeed entirely proper. As these approaches will not improve the discrimination between benign and malignant masses, the preferred practice of the present invention is directed to the use of novel mammographic approaches to define the breast's blood supply, in particular the neovascular micro-vessels, rather than the tissue density. Similar approaches have been addressed using contrast enhanced MRI (Leach, 2001). MRI, however, carries a high price tag, and many patients are excluded including those with pacemakers, aneurysm clips and other implanted magnetic objects, or who are claustrophobic. The preferred practice of the present invention uses a low cost X-ray instrument having exceedingly high resolution and at a greatly reduced dose for breast evaluation. Although this system can be used for routine mammographic imaging, the invention instead concerns the visualization of the neovasculature using a micro-focused, monoenergetic X-ray beam produced by a unique transmission target X-ray tube. Such an approach will not only aid in the detection of breast lesions, but also assist in the discrimination between benign and malignant tumors.

DESCRIPTION OF THE DRAWINGS

Embodiments that illustrate but do not limit the invention will now be described with reference to drawings, in which:

FIG. 2 is a schematic illustration of the dipole flux of the emission shown in FIG. 1a;

By the method of the present invention, malignant tumorous masses may be distinguished from benign masses by visualization of associated neovascular micro-vessels in an X-ray image thereof, which may be a film or a digital image. An alternative, optional procedure to the visualization is to make a count of micro-vessels associated with the suspect mass. The count may be compared with a standard count established previously as an indication of malignancy. A mass may be found to be suspect (i.e. to be regarded as possibly tumorous or cancerous tissue) by means of prior X-ray imaging which detects density differences, or by means of a simultaneous imaging which can employ separate X-ray equipment or utilize the transmission X-ray tube employed to visualize micro-vessels, or by other means such as MRI.

The transmission X-ray tube used in accordance with the present invention is a high efficiency tube enabling reduced linear energy transfer to the breast tissue. Preferably the tube produces a mainly monoenergetic X-ray beam.

Figure 8:
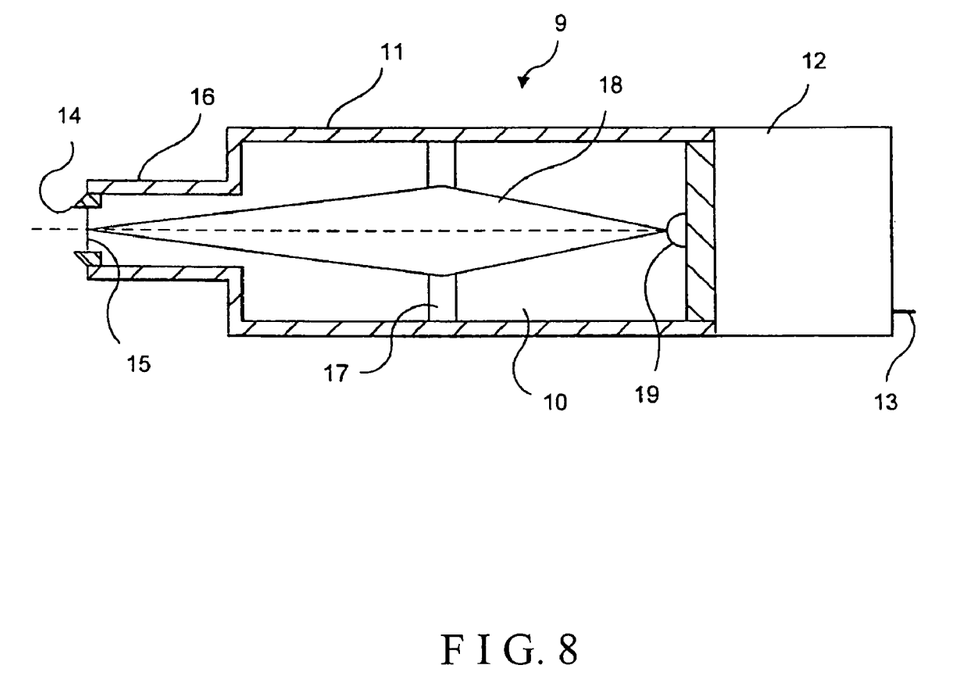
FIG. 8 is a schematic elevational view partly in cross-section of an X-ray tube for use in the present invention.

An x-ray tube according to the present invention is illustrated in FIG. 8. The x-ray tube 9 comprises an evacuated tubular chamber 10 enclosed by a tubular ceramic envelope 11. At one end chamber 10 is connected to end window 14. At its other end, chamber 10 is connected to a power supply 12 which is connected by line 13 to an electrical current supply, now shown, such as a 120 V AC outlet. The power supply may be adjusted so that the energy of x-ray photons from the tube ranges from 4.1 KV to 19 KV for use in alignment of microelectronics, and for medical uses up to 100 KV. Power supply 12 comprises transformers and circuit elements for supplying current to an emitter 19 and to electrostatic lens 17. The components of power supply 12 are contained in a housing which may be made of plastic or metal, and said housing may be filled with an insulating oil.

End window 14 has on its inside surface a metal foil target 15. The end window may be mounted in a tubular extension 16 of smaller diameter than ceramic envelope 11. Tubular extension 16 may be ceramic or metal, is usually stainless steel and, being open to the interior of chamber 10, is evacuated. A typical outside diameter of tubular extension 16 is 5/8 inch. Tubular extension 16 may be surrounded by an annular magnetic coil or lens (not shown). Within chamber 10 is at least one electrostatic lens 17 which focuses e-beam 18.

Contained in chamber 10 is e-beam emitter 19 connected to said power supply 12. The e-beam emitter 19 may comprise a whisker such as a whisker of a tungsten filament. The whisker may have a diameter of several microns and a chemically etched tip of submicron size, from which e-beam 19 is generated. The e-beam spot focused on the target is of similar size as the whisker tip. The e-beam is focused by electrostatic focusing lens 17. Further focusing may be accomplished by the above-mentioned magnetic lens.

Chamber 10, and tubular extension 16 if used, is evacuated by evacuating means such as a vacuum pump; it may be baked at about 350° C. for 9 to 12 hours to de-gas ceramic and metal parts, and it then is sealed.

The x-ray tube of the invention provides an intense x-ray beam emitted from the narrow tubular extension 16. Resulting from the narrow end window design, the thin metal foil 15 and the microfocused emitted x-ray beam, the x-ray tube can be closely placed in proximity to the material or tissue to be exposed to x-rays.

The provided line-emissions may be narrowly tuned, by using a metal foil target of a selected metal and of preselected thickness. Thickness of the foil can range as low as 0.1 μm or below, or can be thicker such as typically 1.0 μm or up to 2.0 μm. The thicker metal foils are used in connection with higher emitted x-ray energies of up to 100 KV.

In one aspect of the invention, an X-ray contrast agent such as an iodinated or chelated gadolinium contrast agent is administered to a patient before imaging breast tissue of the patient with the transmission X-ray tube. When an X-ray contrast agent is employed, preferably an end window X-ray transmission tube is used which produces a mainly monoenergetic x-ray beam of an energy selected for absorption by the contrast agent to provide increased resolution and image contrast.

In the event of use of an iodinated or gadolinium based x-ray contrast agent, it is preferred to use an end window X-ray transmission tube which produces mainly X-ray line-emissions selected for absorption at the K-edge of iodine or gadolinium. The end window comprises a thin metal target on which the electron beam of the X-ray tube impinges. To produce line-emission X-rays adapted for absorption by iodine, a target made of, e.g., lanthanum or cerium may be used, or for absorption by gadolinium, a target made of thulium may be used.

A kit according to the present invention includes both an end window X-ray transmission tube and a supply of an X-ray contrast agent. For reasons given above, the tube comprises a target made of a metal selected to produce X-ray line-emissions having an energy selected for absorption by an element of the contrast agent. In the kit according to the invention, it is preferred that the target comprises lanthanum or cerium and the contrast agent comprises iodine, or for a gadolinium contrast agent, the target companies thulium.

In the following, the rationale of imaging the neovasculature is discussed, followed by a discussion of high efficiency X-ray generation using a transmission X-ray target, and a discussion of thermal management of the X-ray device.

Neovascular Blood Supplies and Carcinoma

It is well known that angiogenesis and neovascularization occurs during the development of malignant tumors and subsequent metastasis (Boudreau et al, 2003; Carmeliet et al, 2000; Folkman, 1992). A solid malignant tumor in its early, prevascular stage does not induce angiogenesis, is limited in size and tends not to metastasize. On the other hand, a vascular tumor induces angiogenesis from host micro-vessels, can rapidly expand its cell population and grow, and often leads to metastasis. Pathohistological studies (Weidner et al. 1991) have correlated both micro-vessel counts and density with metastatic disease. Several factors will stimulate the transition from the prevascular to vascular phase. Hypoxia, genetic changes in tumor cells, increases in the production of vascular endothelial growth factor, and other angiogenic stimulants all contribute to neovascularization.

There is a great need to improve not only the means to diagnose small lesions in the breast, but also to discriminate between malignant and benign tumors at any stage. Since angiogenesis and neovascularization is characteristic of malignancy and not of benign growth, this is an important approach to pursue. MRI (Leach, 2001) of breast tissue can provide three-dimensional identification of multifocal and contralateral disease. Contrast enhanced, functional MRI studies have been performed where, by observing the uptake and washout of these contrasts agents, there has been some success in differentiating between the highly vascular malignant tumors and benign masses.

X-ray mammography has been the gold standard for the diagnosis of breast cancer. Although MRI of the breast has made a surge in recent years, its system and examination costs are approximately an order of magnitude greater than that of X-ray mammography. Also, as mentioned before, women with pacemakers, aneurysm clips and other implanted magnetic objects, or who are claustrophobic, are excluded from MRI.

Breast biopsies are a common practice for the histologic discrimination of malignant versus benign breast lesions. This procedure is expensive and introduces additional physical and emotional trauma to the patient. Thus, there is a strong need not only to improve the ability to diagnose breast lesions using X-ray mammography, but also for X-ray mammography to better discriminate between benign and malignant tumors without the need for biopsy.

The method of the invention uses an end window X-ray transmission tube such as one commercially available from the assignee NanoDynamics-88, Inc., New York, under the Trade Mark "NanoRay".

An X-ray contrast agent preferably is used in the method of the invention, and preferably is an iodinated compound. Iodinated or gadolinium-based compounds have been used extensively as X-ray contrast agents because of their added attenuation. Gadolinium chelates are standard contrast agents for MRI, and have also shown use for X-ray contrast enchancement. Conventional X-ray tubes produce mainly bremsstrahlung (or brem, which is German for slow-down radiation), which yields a broad spectrum of photon energies. In accordance with the present invention there has been developed a unique capability to provide very bright monoenergetic X-ray fluence that can be tuned to the K-absorption edge of iodine or gadolinium. This novel approach markedly increases the photon scattering cross section with iodine or gadolinium by an order of magnitude, greatly increasing its visualization in the vasculature and better defining areas of neovascularization in malignant breast tumors. In the method of the invention, an X-ray target material is selected in relation to the contrast agent which may be used, to provide a desired energy spectrum. Preferably lanthanum (La) is used as the X-ray target material for iodine, or thulium (Tm) for gadolinium. Lanthanum provides a monoenergetic energy spectrum having a $K\alpha^1$ emission of La at slightly above the K-edge of iodine and $K\alpha^2$ at below the K-edge of iodine. The $K\alpha^2$ of La would not have sufficient energy to cause a resonant scattering and would therefore function as a conventional X-ray source. Similarly, both $K\alpha^1$ (34.717 kV) and $K\alpha^2$ (34.276 kV) of cerium can be used for iodine excitation. Thulium would be used as the x-ray target material for gadolinium, where the $K\alpha^1$ emission (50.730 kV of thulium is slightly above the K-edge (50.229 kV) of gadolinium. Using La or Ce as an X-ray target material in combination with iodinated contrast administration, or Tm as an X-ray target material in combination with administration of gadolinium contrast, the NanoRay tube would uniquely provide the ability to visualize the micro-vasculature with high resolution, high sensitivity, and good image contrast.

Diagnosing breast lesions from a mammogram is not an easy task. The rates for false positive and false negative readings are high even for well-trained mammographers. The estimated dose to obtain a mammogram using the presently used mono-energetic, La target X-ray source having a $K\alpha^1$ at about 33 kV or Tm X-ray source having a $K\alpha^1$ at about 51 kV is only about 10 mR compared to about 150 mR for a conventional tube. With the high resolution and efficiency of the NanoRay X-ray apparatus, and its potential to visualize the micro-vasculature of the breast, the NanoRay system would serve at least as a good complement to the routine mammography examination.

High Efficiency Nanoray Tube Using Transmission Target

Since the physics of using transmission targets is somewhat different from that of using a conventional solid target, and there is no comprehensive publication of the subject matter for reference, this discussion begins with a review of e-beam scattering processes. A general review of the X-ray physics can be found in Dyson's book on X-rays in Atomic and Nuclear Physics.

Figure 1:
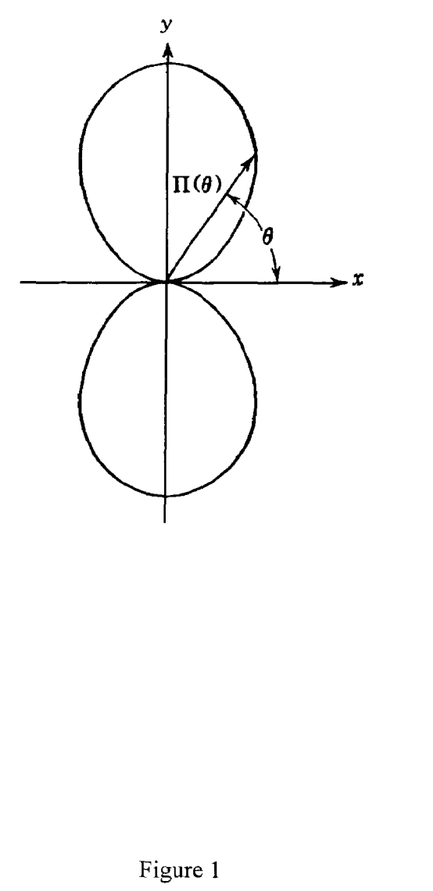
FIG. 1 is a graphical representation of emission of photons in the form of dipole radiation.
Figure 2:
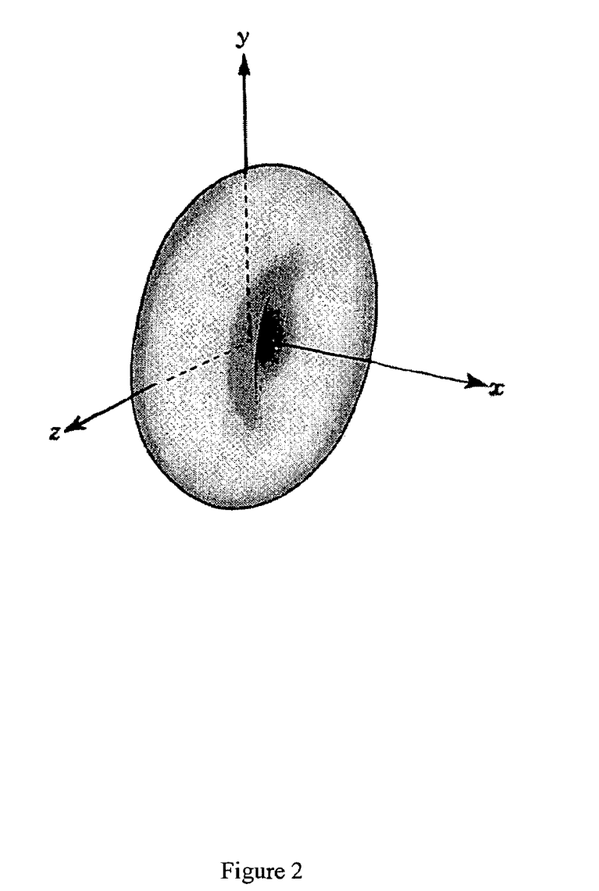

As electrons undergo sudden deceleration, such as that caused by scattering by an atomic nucleus in a metal solid, or are twisted by a wiggler magnetic field in a synchrotron ring, they will emit photons in the form of a dipole radiation as shown in FIG. 1. This dipole flux takes the form of a ring as shown in FIG. 2, which expands outward perpendicular to the e-beam path. Conventional X-ray tubes with a solid target make use of only a small slice of this ring fluence as the tube's output. The remaining X-ray fluence of this emission ring is buried in the X-ray target or must be absorbed by shielding.

Figure 3:
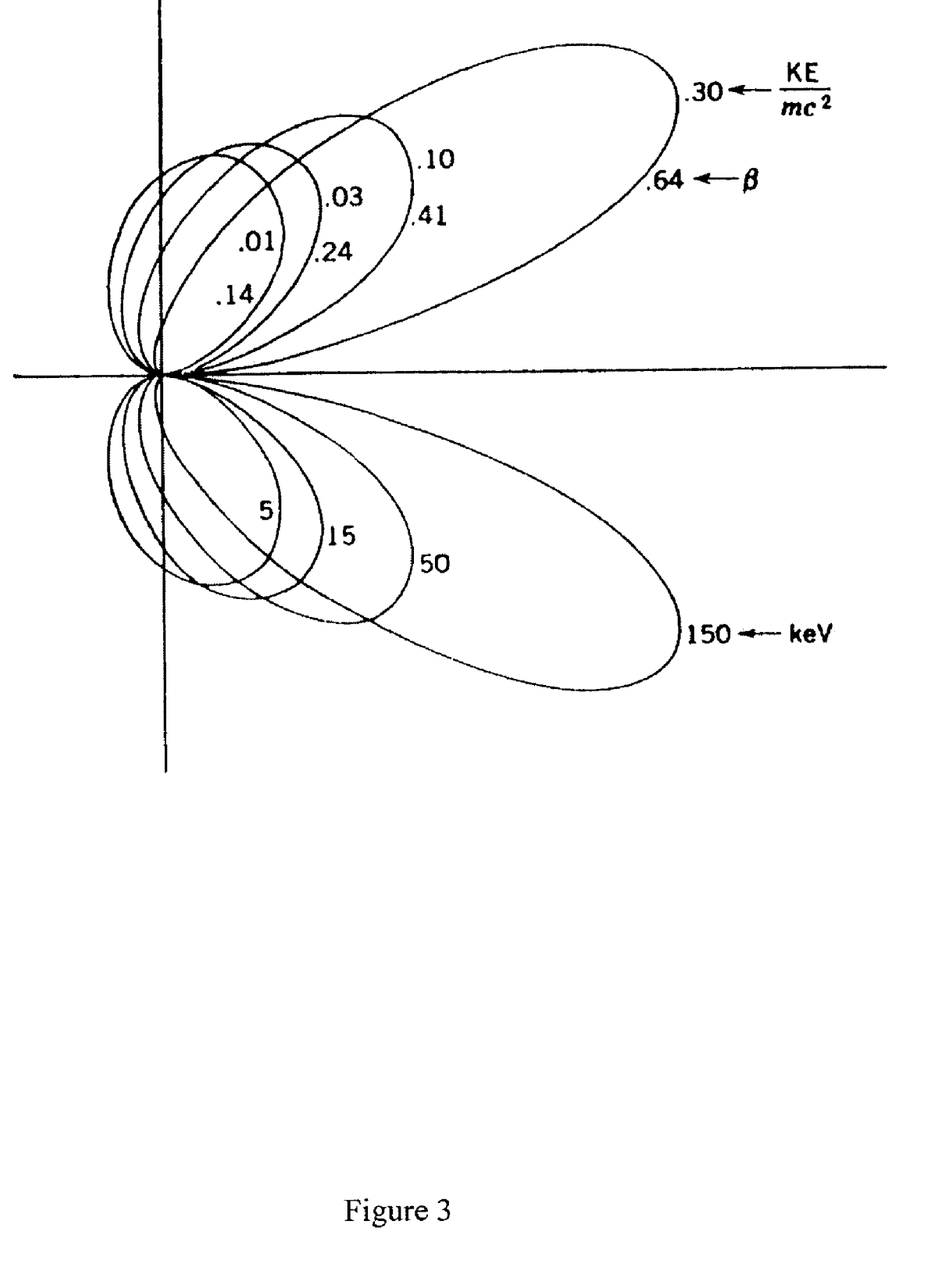
FIG. 3 is a graphical representation of dipole radiation as a function of e-beam energy.

Electrons can quickly become relativistic. For example, at 100 Volts electrons already are at 2% of the speed of light, and 10 kV electrons have a speed of 20% of that of light. As the e-beam energy increases, the dipole radiation undergoes a relativistic transform and moves to a forward direction as shown in FIG. 3. (Robert Leighton, "Principle of Modem Physics", McGraw Hill, pp 413, 1957). Electrons entering a metal solid typically encounter many small angle collisions prior to being scattered by a nucleus that generates X-rays. Since the e-beam path is somewhat randomized, the radiation loci are not nearly as precise as those indicated in FIG. 3. Similar to FIG. 2, each flux at a designated energy would form a radiation ring cone, with the ring cone becoming more forward leaning at higher energies. Conventional tubes use only that portion of the flux components that are perpendicular to the e-beam path. Such components reduce the flux fraction as the energy increases. This relative reduction of perpendicular flux is due to the relativistic transform shown in FIG. 3, and is the main reason that conventional X-ray tubes using a solid target to obtain X-rays perpendicular to the e-beam path are very inefficient.

For a transmission target, the target material is coated on an end-window substrate that can transmit the X-rays with minimal loss. The end-window also conducts the current and the heat, and maintains the vacuum. Most importantly, the transmission target also can serve to filter the X-ray fluence, all in the same X-ray focal spot. A filter can be used to remove unwanted energies from the high-energy brem profile, increasing the proportion of fluorescent line-emissions characteristic of the target material. Transmission targets can be easily designed to produce either mainly brem or predominately line-emissions depending on the target thickness, with the latter at a slightly reduced efficiency.

Figure 4:
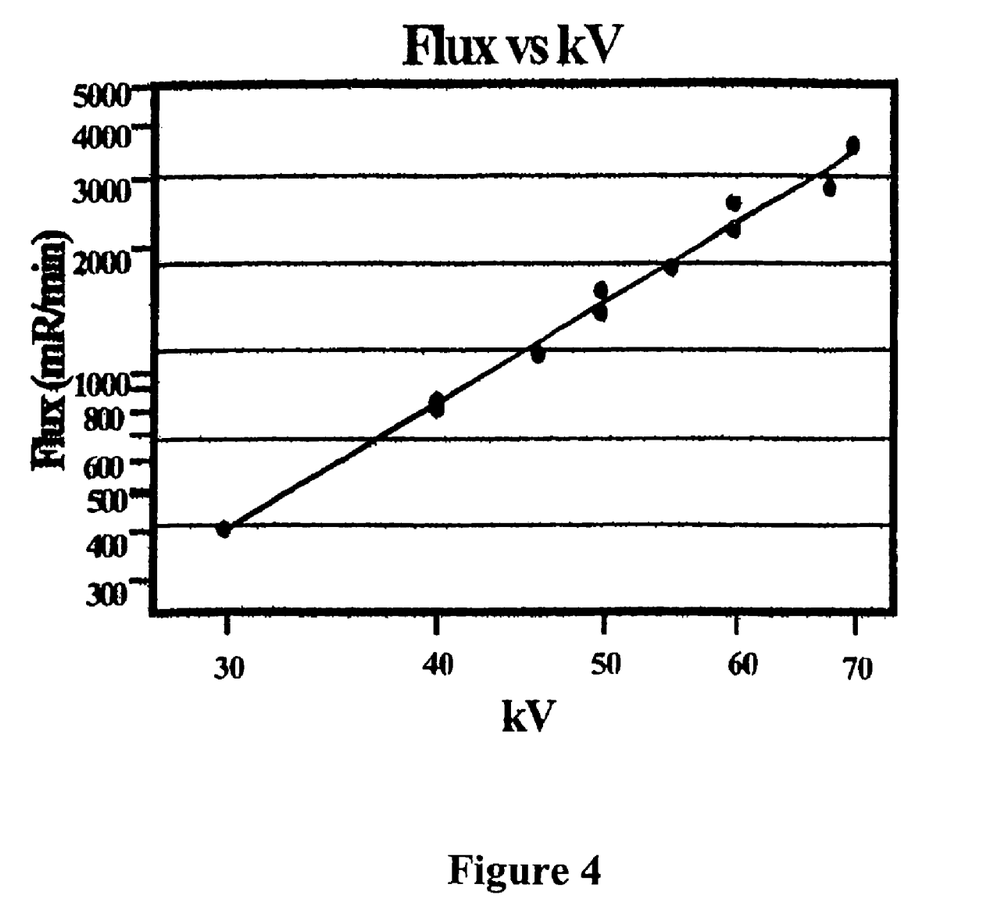
FIG. 4 is a plot of flux as a function of applied voltage.
Figure 5:
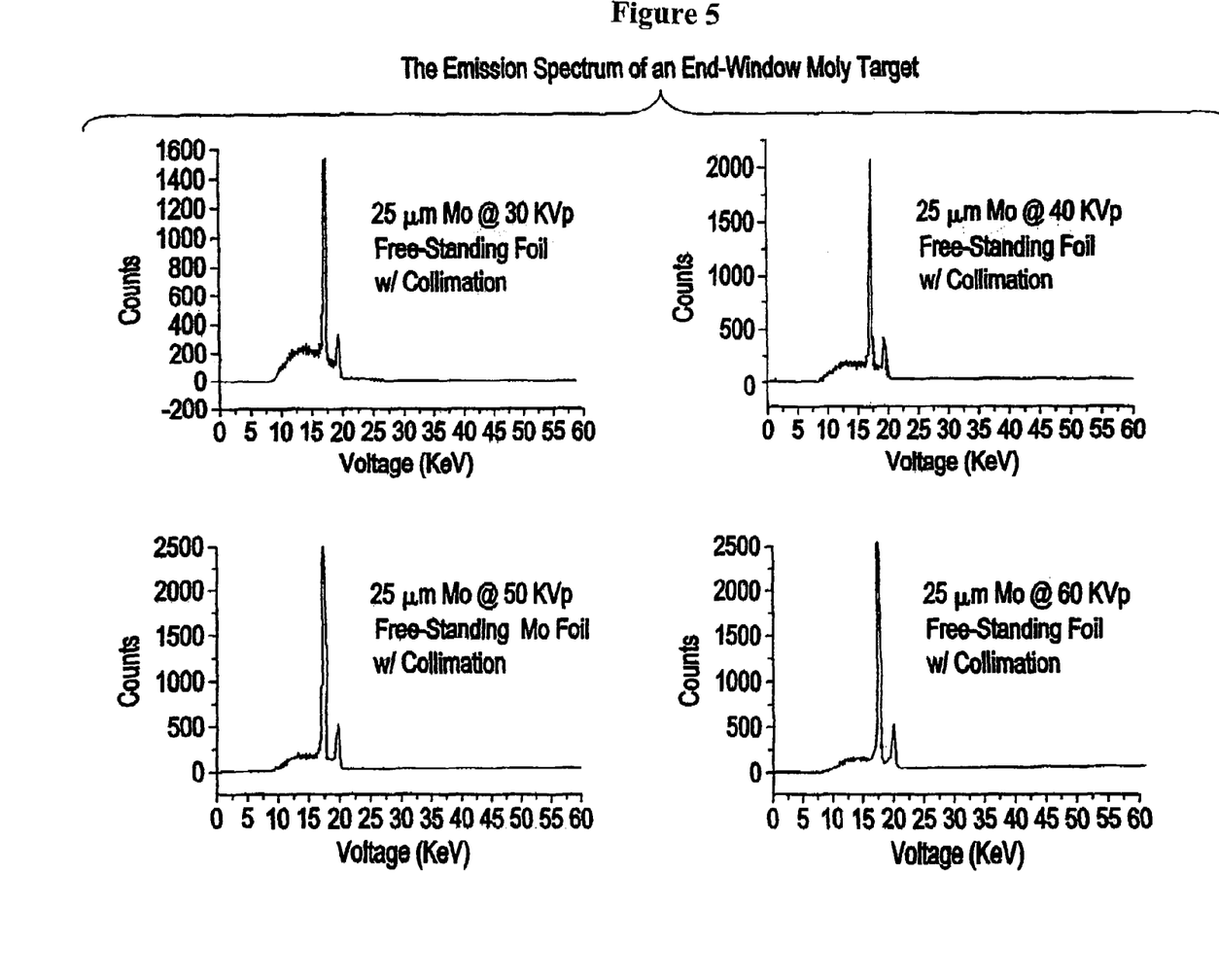
FIG. 5 is a graphical illustration of the line emission of X-rays obtained at four different accelerating voltages for an electron beam impinging a 25 micrometer thick molybdenum target.
Figure 6:
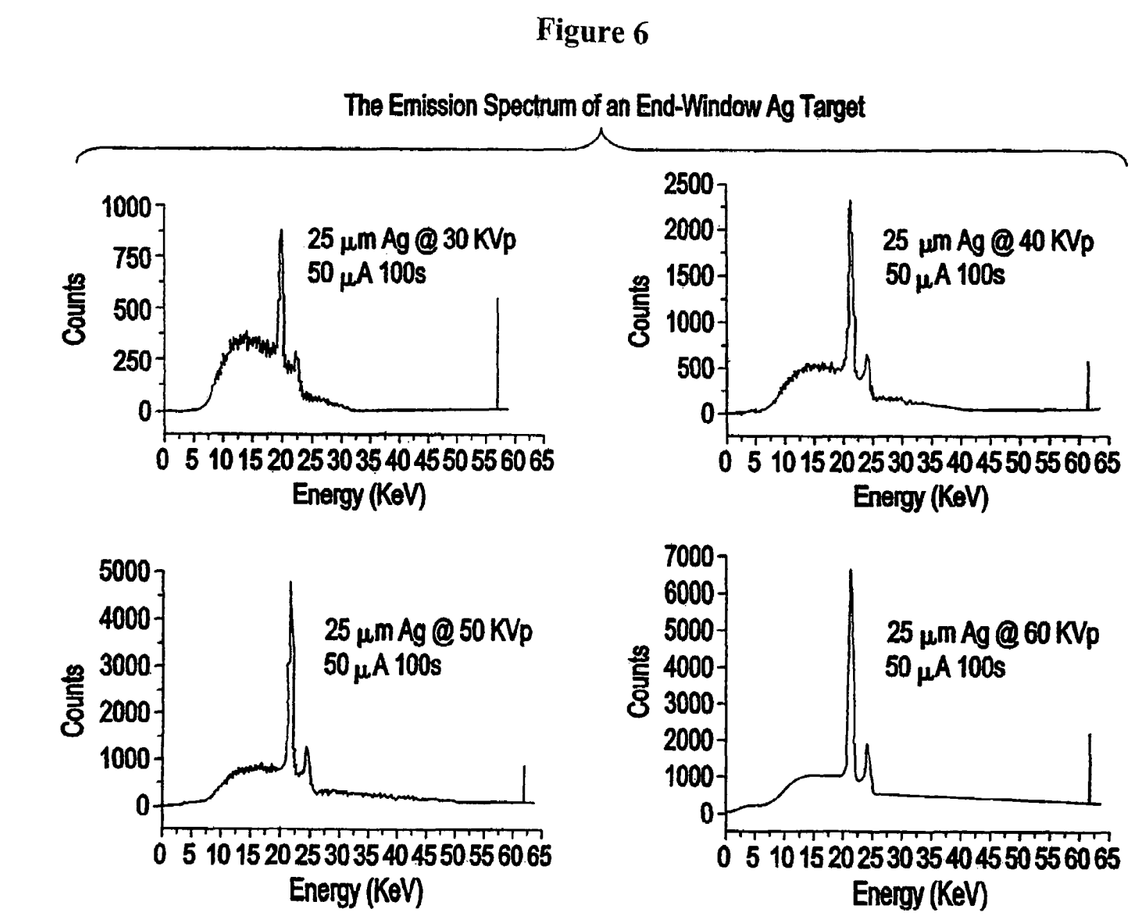
FIG. 6 is a graphical illustration of the line emission of X-rays obtained at four different accelerating voltages for an electron beam impinging a 25 micrometer thick silver target.

In a conventional X-ray tube, the fluence produced increases in proportion to the applied voltage $kV_p$ raised to the 1.7 power. As a result, it is well known in the industry that a tube with higher $kV_p$ is far more efficient. However, for a conventional tube, only a slice of the fluence perpendicular to the e-beam path can be used. For a transmission target, the relationship between $kV_p$ and useable fluence increases to the power of more than 3, depending on the target thickness as shown in FIG. 3, purely because the integration over all the azimuth angles consolidates the fluence. If radiation fluence other than brem is desired, such as fluorescent line-emissions, then the fluence of fluorescent emissions from the transmission target is again homogenized over all solid angles. As a result these line-emissions still produce a much brighter forward emission than the useable fluence from conventional tubes. In transmission targets generating line-emissions, the fluence produced increases as the ratio of the applied voltage raised to the 2.5 power as shown in FIG. 4, which is a significant improvement over conventional tubes whose fluence increases with voltage to the 1.7 power. It should also be noted that this relationship indicates that increasing the brightness by increasing the voltage is far more efficient than increasing the e-beam current while maintaining an unchanged line-emission spectrum, as shown in FIGS. 5 for a Mo target and 6 for a Ag target. In a conventional tube, increasing the voltage by too high a factor would completely alter the beam characteristics, while for emissions from a transmission target designed for line-emission, the fluence can be independent of the $kV_p$. In short, we select a desired value of line-emissions, choose an appropriate element, and arrange it as a transmission target, and raise the e-beam voltage to obtain a very bright tube with exceedingly high efficiency. FIG. 4 shows the measured line-emission fluence of a Ag target at 22 kV as a function of the applied voltage. The spectrum, as shown in FIG. 6, does not shift over a wide range of $kV_p$, only its brightness. It shows a relationship to the 2.5 power of the voltage over the range of 30-70 kV, and is much brighter for the line-emissions at high kV than that obtained from a conventional solid target. Using 90 kV instead of 25 kV, for example, the NanoRay tube can deliver the same X-ray fluence with a power reduction by a factor of 6.8, assuming a reduced power law relationship of $kV_p^{1.5}$ with a thin film target for line-emissions with very bright fluence.

Figure 7:
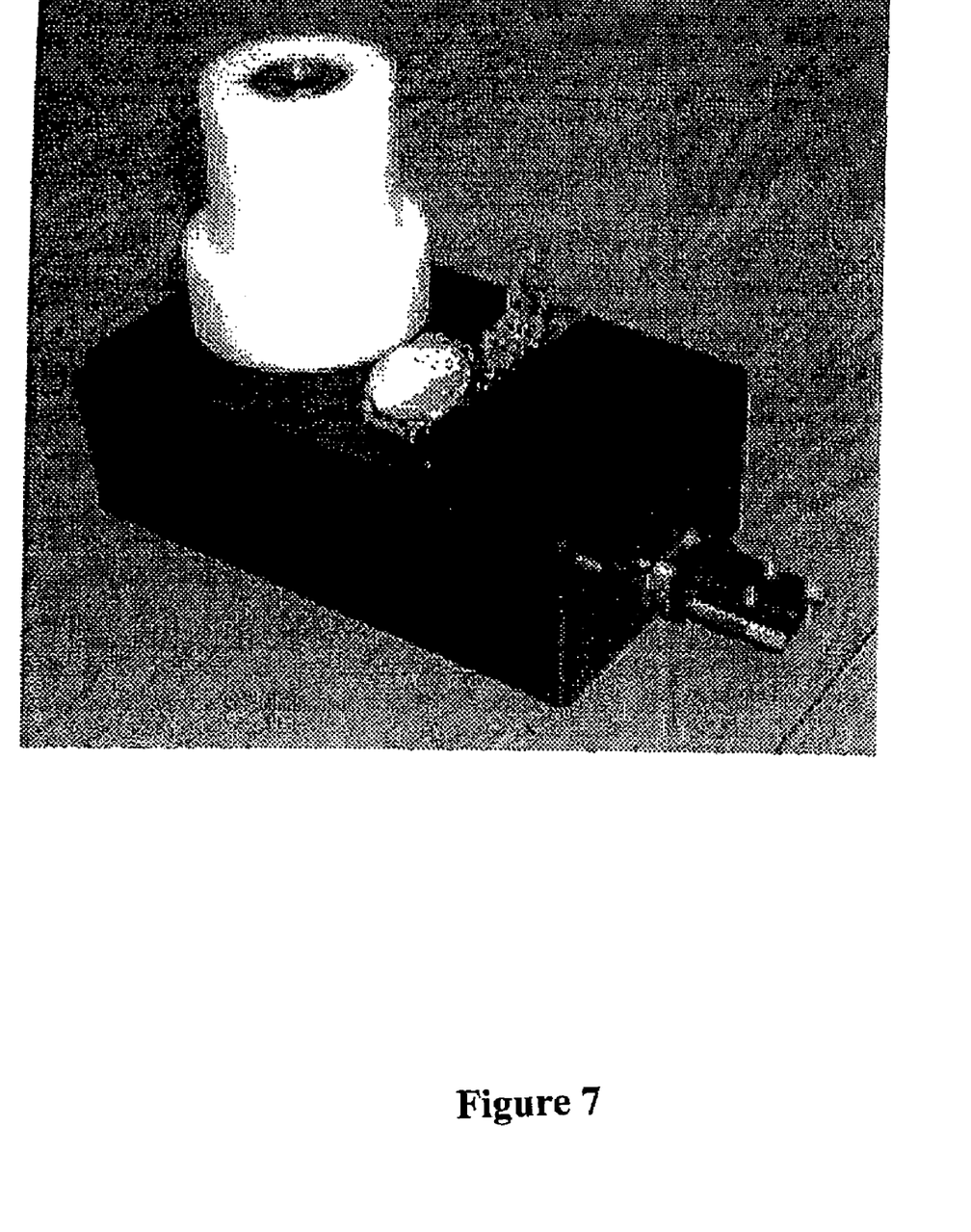
FIG. 7 is a photograph of the NanoRay X-ray tube usable in the method of the present invention.

The reduced e-beam current for the same X-ray fluence obtained using a higher voltage means that there are fewer electrons in the electron beam, which in turn, reduces electrostatic focal dispersion. In addition, a higher beam voltage implies a reduction in the electron traveling time, which again reduces the e-beam dispersion. For the standard ACR accreditation mammographic phantom, fluence of 120 mR at an SID of 60 cm requires for proper exposure about 170 mAs at 25 $kV_p$ using a Mo target. With a transmission Mo or Ag target, using the novel and efficient NanoRay device shown in FIG. 7, there is obtained a similar fluence (SID=60 cm) using only one mAs at 60 kV, and without the need for additional filtering material. The wristwatch shown for scale in FIG. 7 is an indication of the size of the NanoRay device. This NanoRay system weighs only about 3 kg (6 pounds) and can fit inside a shoebox.

A detailed description of an X-ray end window transmission tube is provided in the above mentioned U.S. Pat. No. 5,044,001 and U.S. No. 5,627,871 (compact tube).

Since the NanoRay tube has a broad and uniform output, the tube can be placed much closer to the breast than that required for the conventional tube (60 cm).

As shown in FIG. 7, the NanoRay tube can be constructed to provide mainly line-emissions. For iodinated contrast agents, the designated line-emissions can be selected to reach the K-edge of Iodine at 33.164 kV. The $K\alpha^1$ line of La at 33.440 would do exactly that. But La is difficult to incorporate into a thin film transmission target. On the other hand, Tm with a $K\alpha^1$ of 50.730 kV is stable and easy to incorporate into a transmission X-ray target and use for the K-edge (50.229 kV) of gadolinium. Note that for conventional mammography using 25 kVp, the typical entry dose is 1000 mR and calculated glandular dose for a 50:50 adipose:glandular breast is approximately 200 mR. Thus, the transmitted X-ray fluence through a 4 cm compressed breast is ~4%, while monoenergetic fluence at 33 kV has an absorption coefficient of 0.34 $cm^2/g$ in water as given by NIST, which is equivalent to about 100 $kV_p$ in conventional X-rays, and would transmit ~25% through the same soft tissue. This difference of a factor of 6 implies that in order to sensitize the imager with the same fluence, the NanoRay mammography tube can be operated at a fluence reduction of 6 fold, or an e-beam power reduction of 42 fold under a raised applied e-beam voltage to 90 kV that gives an enhanced efficiency by another factor of 7. The radiation dose to the tissue would be reduced by a factor of 15 or more not only because there would be less total photons, each photon would have a reduced LET by ~25%, but also because of the use of resonant scattering to reach iodine or gadolinium, depending on the iodine or gadolinium concentration, to gain another factor of 2 or more.

Thermal Management Considerations

A highly focused e-beam results in a high power concentration at the focal spot of the target, leading to a problem of heat dissipation, which must be resolved. First there is considered heat distribution without active thermal management, and then consideration of heat removal from the target material.

Transmission targets are typically made of a thin metal film, say 10 mm, coated on a Be substrate, typically one mm thick. The target film transmits its heat instantly through the thin film to the Be material which has a conductivity of K=1.68 W/° C.-cm. For a given amount of power deposition W (in watts) to be conducted over a semisphere of area $2\pi r^2$, the conductivity relationship follows:

$$W = \frac{K \cdot 2\pi r^2 dT}{dr}$$

Integrating from $r_0$ to $r_1$, where $r_0$ is the radius of the beam spot size and $r_1$ the integration limit, which can be the substrate thickness, where $r_1 >> r_0$, the temperature rise $\Delta T$ becomes $$\Delta T = \int_{r_0}^{r_1} \frac{W dr}{K \cdot 2\pi r^2} = \frac{W}{2\pi K}\left(\frac{1}{r_0} - \frac{1}{r_1}\right) = \frac{W}{2\pi K r_0}$$

For Be, $2\pi K \cong 10$, and the spot size $d=2r_0=W/5\Delta T$). Assuming the upper limit of temperature increase is 500EC, then each watt of power would require 4 µm of spot size diameter to be able to conduct the heat away, assuming there is no black body radiation or active cooling across the Be substrate layer. In reality, there is obtained a practical limit of approximately 1 µm per watt of power for power levels under 100 watts. For power levels well over 100 watts, however, active thermal management would be required to redistribute the thermal load away from the anode target. Note that because of the higher efficiency of the X-ray generation from a transmission target, a mere 100 watt thermal load here would already suffice for most medical imaging needs. The NanoRay tube covers, of course, a far larger area of solid angles and produces far more total X-ray fluence. Oil injection in front of the Be layer, for example, will carry heat away very efficiently up to several hundred watts. For power levels over 1 kW however, heat pipes using evacuated metal tubes may be required. Such heat pipes contain liquid, which evaporates at the hot spot and condenses at a cooler place. The condensed liquid is brought back to the hot spot with a wetted whisker. Such a heat pipe design could handle thermal loads two orders of magnitude higher than a solid copper tube of the same dimension.

The thermal load of a conventional mammographic tube with rotating target varies between 3.5-5 kW, with an X-ray focal spot size at 300 mm for routine screening and 100 μm for high resolution evaluation. As mentioned earlier, when using a relatively hard, monoenergetic photon beam of 33 kV, the X-ray fluence reaching the imager will be ~25% over a 4 cm soft tissue instead of 4% fluence when using a conventional tube at 25 $kV_p$. This factor of 6 allows the detector to receive the same amount of X-ray fluence with a reduced tube output by the same factor. In reality, the NanoRay tube can gain another factor of 7 by using a $kV_p$ at 90 kV instead of 25 kV, and with appropriate concentration of iodinated or gadolinium contrast agent for another factor of 2 or more in the X-ray fluence required, resulting in an e-beam power of one hundred fold reduction, to only 35-50 watts. Under such a load, the NanoRay tube can readily be cooled by air with an X-ray focal spot under 100 μm.

EXAMPLE

Selection of FDA Approved Iodinated or Gadolinium Based Contrast Agents

None of the FDA approved iodinated contrast agents are analogs of the building blocks of DNA, so that the risk of mutagenic cell uptake is low. These iodinated contrast agents contain different molar concentration of iodine, and since in one approach the method of the invention aims for atomic inner K-shell resonant scattering of iodine, there is a need for the highest concentration of iodine possible with a very low in vivo toxicity. Agents such as iotrolan (with 5 iodine atoms per molecule) and iodixanol (also 5 iodine atoms), both are water-soluble, have low toxicity, are low-osmolar and are marketed by Amersham, now a division of GE, are available and can be prepared with various dilutions for their X-ray absorption selection. Any of the FDA approved gadolinium based contrast agents can be used for the invention. These contrast agents can be tested with photons at above and below the iodine or gadolinium K-edge, by selecting X-ray tubes with different target elements. For example, Ag with a Kα at 22 kV can be used for irradiation below the K-edge of iodine.

Construction of the Thin Film La, Ce or Tm Target

Lanthanum and cerium are pyrophoric elements and cannot readily be handled in the fabrication process. La or Ce must be kept under an inert gas and be sputtered in a sputtering chamber for thin film deposition, onto a suitable substrate. Thulium, however, is stable in air and can be readily sputtered onto a suitable substrate. The substrate e.g. can be either Be or Al, and the filter function of aluminum for conventional X-ray fluence to reduce the soft brem can be combined with the target by sputtering the La, Ce or Tm onto an Al substrate.

Construction of the Micro-Focused Nanoray Tube with the La, Ce or Tm Target

The target material may first be tested in an experimental X-ray station and the emission spectrum obtained. Adjustments, such as the substrate thickness, target film thickness, etc. can be made in order to obtain a very bright $K\alpha^1$ of La emission or K-lines of Ce at approximately 80 kV. For bright Tm line emissions, a higher tube voltage of at least 120 kV is necessary. The tested end-window La, Ce or Tm target can then be incorporated into a permanent NanoRay tube as shown in FIG. 7.

Imaging the Iodinated or Gadolinium Agents with La or Tm Line-Emissions, Respectively For testing, the iodinated or gadolinium based contrast agent is introduced in capillary tubes with various dilutions, and their images obtained under a range of fluence levels. These images are compared with the anticipated in vivo level of the injected contrast agents, to determine dosages.

Industrial Potential and Advantages

There are approximately 15,000 mammographic instruments operating in the U.S. with each having a patient load of ~5,500 per year. They provide about 80 million examinations at a cost of ~$7 billion excluding biopsies and other patient care costs. The European market size is roughly equal to that of the U.S., while the third world markets are expanding rapidly.

Designed to image the neovasculature, use of the NanoRay device with contrast administration is not meant to improve the performance of the current mammographic modalities, under digital as well as film imagers; the NanoRay device would complement existing instruments as well as providing novel mammographic techniques at very low doses. After all, an inexpensive 3 kg (6 lb) unit with an estimated dose reduction of 93% can certainly serve many users, particularly those before the age of 50.

While the NanoRay instrument is small, light, and less costly, it need not replace a saturated conventional market but provides a new mode of service. The NanoRay device can readily be made portable and serve in nursing homes, for example, where the transportation of patients to clinics has been an expensive and difficult endeavor.

Permutations and variations of the invention as will occur to those of ordinary skill in the art are within the scope of the following claims.

The invention claimed is:

1. A method for examining breast tissue of a patient for abnormalities, the method comprising the steps of:
    (a) providing an end window X-ray transmission tube comprising a lanthanum, cerium or thulium target that produces mainly X-ray line-emissions selected for absorption at the K-edge of iodine or gadolinium, said X-ray transmission tube having a focal spot under 100 μm;
    (b) imaging the breast tissue to produce a film or a digital image with the mainly X-ray line-emissions from the end window X-ray transmission tube after first administering to the patient an X-ray contrast agent for the breast tissue, said contrast agent being an iodinated contrast agent if the target is lanthanum or cerium or a gadolinium based contrast agent if the target is thulium such that the contrast agent absorbs the mainly X-ray line-emissions at the K-edge of iodine or gadolinium whereby the imaging of the breast tissue with the mainly X-ray line-emissions after administration of the contrast agent provides sufficient resolution and image contrast for measuring density of neovascular micro-vessels associated with a suspected tumorous mass;
    (c) viewing the film or digital image and measuring the density of neovascular micro-vessels if present in the film or digital image; and (d) biopsying the breast tissue if and only if the viewing and measurement of density suggests the presence of a suspected tumorous mass.

2. The method according to claim 1, wherein the measurement of density comprises comparing the density of the neovascular micro-vessels with a standard density indicative of malignancy.

3. The method according to claim 1, wherein the contrast agent is an iodinated contrast agent and the end window X-ray transmission tube comprises a lanthanum or cerium target.

4. The method according to claim 3, wherein the contrast agent is iotrolan.

5. The method according to claim 1, wherein the contrast agent is a gadolinium based contrast agent and the end window X-ray tube comprises a thulium target.

6. A method for examining breast tissue of a patient comprising:
(a) providing a kit for mammography comprising (i) a high-efficiency, end window X-ray transmission tube comprising a lanthanum or cerium target, said X-ray transmission tube producing mainly X-ray line emissions selected for absorption at the K-edge of iodine and having a focal spot under 100 μm; and (ii) a supply of X-ray contrast agent, said contrast agent being an iodinated contrast agent which absorbs the mainly X-ray line emissions produced by the X-ray transmission tube at the K-edge of iodine, wherein the end window X-ray transmission tube provides a bright monoenergetic X-ray fluence that, upon imaging of breast tissue with the mainly X-ray line-emissions after administration of the contrast agent, causes photon resonant scattering with iodine that produces sufficient resolution and image contrast for measuring a density of neovascular micro-vessels associated with a suspected tumorous mass in the breast tissue;
(b) imaging the breast tissue to produce a film or digital image with the mainly X-ray line-emissions from the end window X-ray transmission tube after first administering the iodinated contrast agent to the breast tissue such that the contrast agent absorbs the mainly X-ray line-emissions at the K-edge of iodine whereby the imaging of the breast tissue with the mainly X-ray line-emissions after administration of the contrast agent provides sufficient resolution and image contrast for measuring the density of neovascular micro-vessels associated with a suspected tumorous mass in the breast tissue;
(c) measuring the density of neovascular micro-vessels if present in the film or digital image of the breast tissue; and
(d) biopsying the breast tissue if and only if the measurement of density suggests the presence of a suspected tumorous mass.

7. The method according to claim 6, wherein the measuring comprises comparing the density of the neovascular micro-vessels with a standard density indicative of malignancy.

8. The method according to claim 6, wherein the contrast agent is iotrolan.

9. A method for examining breast tissue of a patient comprising:
(a) providing a kit for mammography comprising (i) a high-efficiency, end window X-ray transmission tube comprising a thulium target, said X-ray transmission tube producing mainly X-ray line emissions selected for absorption at the K-edge of gadolinium and having a focal spot under 100 μm; and (ii) a supply of X-ray contrast agent, said contrast agent being a gadolinium based contrast agent which absorbs the mainly X-ray line emissions produced by the X-ray transmission tube at the K-edge of gadolinium, wherein the end window X-ray transmission tube provides a bright monoenergetic X-ray fluence that, upon imaging of breast tissue with the mainly X-ray line-emissions after administration of the contrast agent, causes photon resonant scattering with gadolinium that produces sufficient resolution and image contrast for measuring a density of neovascular micro-vessels associated with a suspected tumorous mass in the breast tissue;
(b) imaging the breast tissue to produce a film or a digital image with the mainly X-ray line-emissions from the end window X-ray transmission tube after first administering the iodinated contrast agent to the breast tissue such that the contrast agent absorbs the mainly X-ray line-emissions at the K-edge of iodine whereby the imaging of the breast tissue with the mainly X-ray line-emissions after administration of the contrast agent provides sufficient resolution and image contrast for measuring the density of neovascular micro-vessels associated with a suspected tumorous mass in the breast tissue;
(c) measuring the density of neovascular micro-vessels if present in the film or digital image of the breast tissue; and
(d) biopsying the breast tissue if and only if the measurement of density suggests the presence of a suspected tumorous mass.

10. The method according to claim 9, wherein the measuring comprises comparing the density of the neovascular micro-vessels With a standard density indicative of malignancy.

* * * * *